United States Patent
Lo et al.

(10) Patent No.: US 11,923,046 B2
(45) Date of Patent: *Mar. 5, 2024

(54) NONINVASIVE PRENATAL MOLECULAR KARYOTYPING FROM MATERNAL PLASMA

(71) Applicant: The Chinese University of Hong Kong, Shatin (HK)

(72) Inventors: Yuk Ming Dennis Lo, Hong Kong (CN); Kwan Chee Chan, Hong Kong (CN); Peiyong Jiang, Hong Kong (CN); Cheuk Yin Jandy Yu, Hong Kong (CN); Rossa Wai Kwun Chiu, Hong Kong (CN)

(73) Assignee: The Chinese University of Hong Kong, Shatin (HK)

( * ) Notice: Subject to any disclaimer, the term of this patent is extended or adjusted under 35 U.S.C. 154(b) by 1064 days.

This patent is subject to a terminal disclaimer.

(21) Appl. No.: 16/785,094

(22) Filed: Feb. 7, 2020

(65) Prior Publication Data

US 2020/0176075 A1    Jun. 4, 2020

Related U.S. Application Data

(63) Continuation of application No. 13/837,776, filed on Mar. 15, 2013, now Pat. No. 10,643,738.

(60) Provisional application No. 61/751,213, filed on Jan. 10, 2013.

(51) Int. Cl.
　　*G16B 20/10* (2019.01)
　　*G16B 20/00* (2019.01)
　　*G16B 30/10* (2019.01)

(52) U.S. Cl.
　　CPC ............ *G16B 20/10* (2019.02); *G16B 20/00* (2019.02); *G16B 30/10* (2019.02)

(58) Field of Classification Search
　　None
　　See application file for complete search history.

(56) References Cited

U.S. PATENT DOCUMENTS

| | | | |
|---|---|---|---|
| 7,888,017 | B2 | 2/2011 | Quake et al. |
| 8,008,018 | B2 | 8/2011 | Quake et al. |
| 8,195,415 | B2 | 6/2012 | Fan et al. |
| 2002/0164816 | A1 | 11/2002 | Quake |
| 2007/0202525 | A1 | 8/2007 | Quake et al. |
| 2008/0096216 | A1 | 4/2008 | Quake |
| 2009/0029377 | A1 | 1/2009 | Lo et al. |
| 2009/0170114 | A1 | 7/2009 | Quake et al. |
| 2010/0112575 | A1 | 5/2010 | Fan et al. |
| 2010/0112590 | A1 | 5/2010 | Lo et al. |
| 2011/0201507 | A1 | 8/2011 | Rava et al. |
| 2012/0237928 | A1 | 9/2012 | Rava et al. |
| 2012/0270739 | A1 | 10/2012 | Rava et al. |
| 2013/0040824 | A1 | 2/2013 | Lo et al. |

FOREIGN PATENT DOCUMENTS

| | | |
|---|---|---|
| CN | 101849236 | 9/2010 |
| WO | 2007092473 | 8/2007 |
| WO | 2011057094 A1 | 5/2011 |
| WO | 2012071621 A1 | 6/2012 |

OTHER PUBLICATIONS

Janevski et al. "Effective normalization for number variation detection from whole genome sequencing." BMC Genomics, vol. 13(Suppl 6):S16, pp. 1-11. (Year: 2012).*
Przybytkowski et al. "The use of ultra-dense array CGH analysis for the discovery of micro-copy No. alterations and gene fusions in the cancer genome." BMC Medical Genomics, vol. 4:16, pp. 1-13. (Year: 2011).*
U.S. Appl. No. 13/837,776, Advisory Action dated May 15, 2017, 6 pages.
U.S. Appl. No. 13/837,776, Final Office Action dated May 13, 2016, 11 pages.
U.S. Appl. No. 13/837,776, Final Office Action dated Nov. 6, 2019, 16 pages.
U.S. Appl. No. 13/837,776, Final Office Action dated Feb. 9, 2017, 19 pages.
U.S. Appl. No. 13/837,776, Final Office Action dated Dec. 20, 2017, 23 pages.
U.S. Appl. No. 13/837,776, Non-Final Office Action dated Sep. 26, 2018, 23 pages.
U.S. Appl. No. 13/837,776, Non-Final Office Action dated Jul. 3, 2019, 14 pages.
U.S. Appl. No. 13/837,776, Non-Final Office Action dated Oct. 2, 2015, 14 pages.
U.S. Appl. No. 13/837,776, Non-Final Office Action dated Mar. 1, 2019, 15 pages.
U.S. Appl. No. 13/837,776, Non-Final Office Action dated Sep. 6, 2016, 15 pages.
U.S. Appl. No. 13/837,776, Non-Final Office Action dated Jul. 12, 2017, 23 pages.
Abyzov et al., CNVnator: An Approach to Discover, Genotype, and Characterize Typical and Atypical CNVs from Family and Population Genome Sequencing, Genome Research, vol. 21, No. 6, Feb. 7, 2011, pp. 974-984.

(Continued)

*Primary Examiner* — John S Brusca
*Assistant Examiner* — Steven W. Bailey
(74) *Attorney, Agent, or Firm* — Kilpatrick Townsend & Stockton LLP

(57) ABSTRACT

Disclosed herein are methods, systems, and apparatus for detecting microamplifications or microdeletions in the genome of a fetus. In some embodiments, the method comprises receiving sequence tags for each of a plurality of DNA fragments in a biological sample; determining genomic positions for the sequence tags; determining whether the density of DNA in each of a plurality of genomic regions is aberrantly high or low; identifying as a microamplification a set of consecutive genomic regions having aberrantly high density; and identifying as a microdeletion a set of consecutive genomic regions having aberrantly low density. The biological sample may be a blood sample obtained noninvasively from a female subject pregnant with the fetus.

22 Claims, 9 Drawing Sheets

(56) References Cited

OTHER PUBLICATIONS

Alkan et al., Personalized Number and Segmental Duplication Maps Using Next-Generation Sequencing, Nature Genetics, vol. 41, No. 10 and Supplementary Information, Oct. 30, 2009, pp. 1061-1067 & pp. 1-68.
Australian Application No. 2014205038, First Examiner Report dated Sep. 9, 2016, 3 pages.
Australian Application No. 2014205038, Second Examination Report dated Dec. 14, 2016, 4 pages.
Bianchi et al., Genome-Wide Fetal Aneuploidy Detection by Maternal Plasma DNA Sequencing, Obstetrics & Gynecology, vol. 119, No. 5, May 2012, pp. 890-901.
Canadian Application No. 2,895,206, Office Action dated Sep. 16, 2019, 6 pages.
Chan et al., Cancer Genome Scanning in Plasma: Detection of Tumor-Associated Number Aberrations, Single-Nucleotide Variants, and Tumoral Heterogeneity by Massively Parallel Sequencing, Clinical Chemistry, vol. 59, No. 1, Jan. 2013, pp. 211-224.
Chen et al., Noninvasive Prenatal Diagnosis of Fetal Trisomy 18 and Trisomy 13 by Maternal Plasma DNA Sequencing, Public Library of Science One, vol. 6, No. 7, Jul. 6, 2011, pp. 1-7.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences of the United States of America, vol. 105, No. 51, Dec. 23, 2008, pp. 20458-20463.
Chinese Application No. 201480003986.6, Office Action dated Mar. 30, 2017, 14 pages (7 pages of Original Document and 7 pages of English Translation).
De Ligt et al., Massively Parallel Sequencing for Noninvasive Prenatal Diagnosis of Partial Fetal Aneuploidies, Prenatal Diagnosis, vol. 32, No. 1, 2012, p. 59.
European Application No. 14737956.4, Extended European Search Report dated Jul. 28, 2016, 12 pages.
European Application No. 14737956.4, Office Action dated May 22, 2019, 6 pages.
Fan et al., Analysis of the Size Distributions of Fetal and Maternal Cell-Free DNA by Paired-End Sequencing, Clinical Chemistry, vol. 56, No. 8, Aug. 2010, pp. 1279-1286.
Fan et al., Detection of Aneuploidy with Digital Polymerase Chain Reaction, Analytical Chemistry, American Chemical Society, vol. 79, No. 19, Oct. 1, 2007, pp. 7576-7579.
Fan et al., Microfluidic Digital PCR Enables Rapid Prenatal Diagnosis of Fetal Aneuploidy, American Journal of Obstetrics & Gynecology, May 2009, pp. 543e1-543e7.
Fan et al., Noninvasive Diagnosis of Fetal Aneuploidy by Shotgun Sequencing DNA from Maternal Blood, Proceedings National Academy of Sciences, vol. 105, No. 42, Oct. 21, 2008, pp. 16266-16271.
Fan et al., Non-Invasive Prenatal Measurement of the Fetal Genome, Supplementary Information, Nature, vol. 487, 2012, pp. 1-19.
Fan et al., Non-Invasive Prenatal Measurement of the Fetal Genome, Nature, vol. 487, No. 7407, Jul. 19, 2012, pp. 1-7.
Fan et al., Sensitivity of Noninvasive Prenatal Detection of Fetal Aneuploidy from Maternal Plasma Using Shotgun Sequencing is Limited Only by Counting Statistics, Public Library of Science One, vol. 5, No. 5, May 3, 2010, pp. 1-7.
Harris et al., Single-Molecule DNA Sequencing of a Viral Genome, Science, vol. 320, Apr. 4, 2008, pp. 106-109.
Jensen et al., Detection of Microdeletion 22q11.2 in a Fetus by Next-Generation Sequencing of Maternal Plasma, Clinical Chemistry, vol. 58, No. 7, Dec. 31, 2012, pp. 1148-1151.
Japanese Application No. 2015-551935, Office Action dated Jun. 28, 2016, 15 pages (6 pages of Original Document and 9 pages of English Translation).
Japanese Application No. 2015-551935, Office Action dated Feb. 14, 2017, 8 pages (3 pages of Original Document and 5 pages of English Translation).
Japanese Application No. 2017-225951, Office Action dated Sep. 24, 2019, 11 pages (4 pages of Original Document and 7 pages of English Translation).
Japanese Application No. 2017-225951, Office Action dated Jan. 8, 2019, 9 pages (3 pages of Original Document and 6 pages of English Translation).
Japanese Application No. 2020-008732, Office Action dated Mar. 30, 2021, 8 pages (3 pages of Original Document and 5 pages of English Translation).
KR10-2015-7017193, Office Action dated Jun. 26, 2017, 12 pages (6 pages of Original Document and 6 pages of English Translation).
KR10-2015-7017193, Office Action dated Jan. 19, 2018, 13 pages (6 pages of Original Document and 7 pages of English Translation).
KR10-2019-7004749, Office Action dated Apr. 30, 2019, 12 pages (6 pages of Original Document and 6 pages of English Translation).
KR10-2019-7031373, Office Action dated Feb. 17, 2020, 9 pages (5 pages of Original Document and 4 pages of English Translation).
Lo et al., Genomic Analysis of Fetal Nucleic Acids in Maternal Blood, Annual Review of Genomics and Human Genetics, vol. 13, No. 1, May 2012, pp. 285-306.
Lo et al., Maternal Plasma DNA Sequencing Reveals the Genome-Wide Genetic and Mutational Profile of the Fetus, Science Translational Medicine, vol. 2, No. 61, Dec. 8, 2010, pp. 1-13.
Lo, Non-Invasive Prenatal Diagnosis by Massively Parallel Sequencing of Maternal Plasma DNA, Open Biol., vol. 2, No. 6, Jun. 2012, 5 pages.
Lo et al., Presence of Fetal DNA in Maternal Plasma and Serum, The Lancet, vol. 350, No. 9076, Aug. 16, 1997, pp. 485-487.
International Application No. PCT/AU2014/000012, International Search Report and Written Opinion dated Mar. 4, 2014, 12 pages.
Peters et al., Noninvasive Prenatal Diagnosis of a Fetal Microdeletion Syndrome, New England Journal of Medicine, vol. 365, No. 19, Nov. 10, 2011, 3 pages.
Singapore Application No. 11201504795P, Further Written Opinion dated Jul. 10, 2017, 7 pages.
Singapore Application No. 11201504795P, Written Opinion dated Jul. 26, 2016, 6 pages.
Srinivasan et al., Noninvasive Detection of Fetal Subchromosome Abnormalities Via Deep Sequencing of Maternal Plasma, The American Journal of Human Genetics, vol. 92, No. 2, Feb. 7, 2013, pp. 167-176.
Wright et al., The Use of Cell-Free Fetal Nucleic Acids in Maternal Blood for Non-Invasive Prenatal Diagnosis, Human Reproduction Update, vol. 15, No. 1, Jan. 2009, pp. 139-151.

* cited by examiner

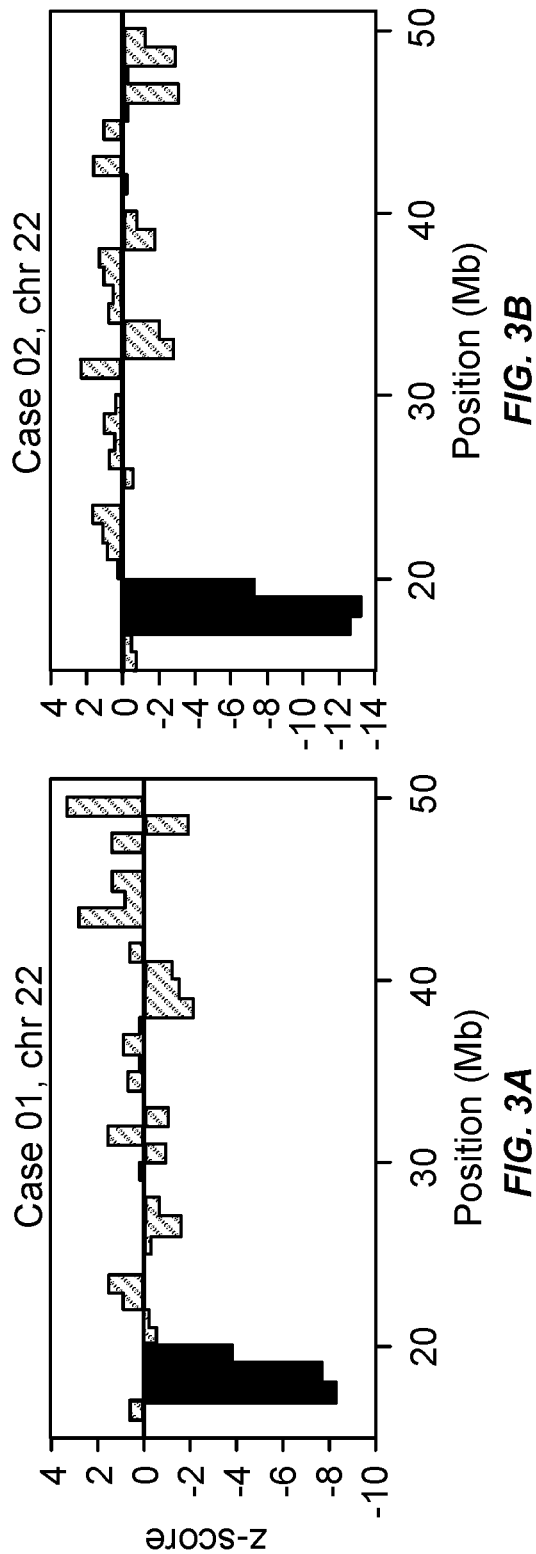
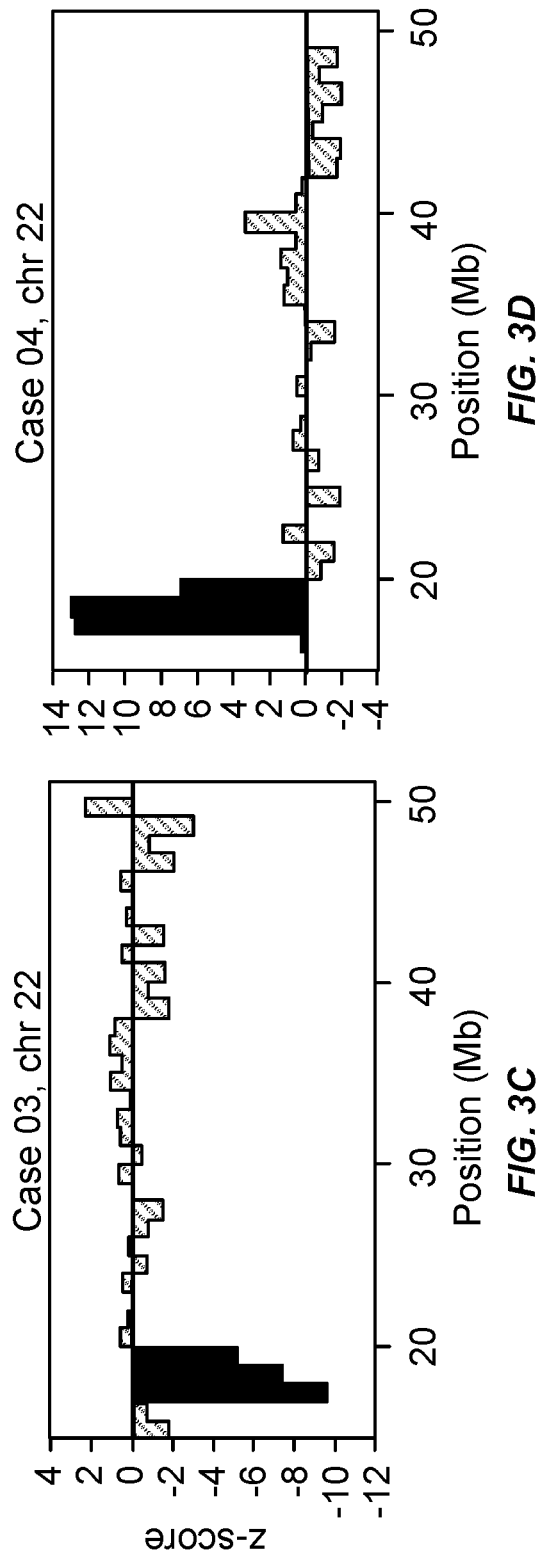
FIG. 3A
FIG. 3B
FIG. 3C
FIG. 3D

| Case | Fetal sex | Fetal DNA percentage | |
|---|---|---|---|
| | | By genomic representation of the affected chromosomal region(s) | By chr Y approach[a] |
| 01 | F | 10.5% | — |
| 02 | M | 17.4% | 21.5% |
| 03 | M | 9.2% | 13.7% |
| 04 | M | 17.8% | 20.3% |
| 05[b] | F | — | — |
| 06 | F | 10.9 %/13.4%[c] | — |

FIG. 5

| Diagnostic sensitivity | | Diagnostic resolution | | |
|---|---|---|---|---|
| | | 3 Mb | 2 Mb | 1 Mb |
| 95% | No. of molecules required in each bin | 42,000 | 42,000 | 42,000 |
| | Total no. of bins for the whole genome | 3,000 | 4,500 | 9,000 |
| | Total no. of molecules required for the whole genome | 125 million | 192 million | 380 million |
| 99% | No. of molecules required in each bin | 53,000 | 53,000 | 53,000 |
| | Total no. of bins for the whole genome | 3,000 | 4,500 | 9,000 |
| | Total no. of molecules required for the whole genome | 160 million | 240 million | 480 million |

*FIG. 7*

| Case no. | Gestational age at plasma collection (weeks) | Plasma sampling relative to invasive procedure | Invasive procedure | Chromosomal aberration | Methods used to confirm karyotype |
|---|---|---|---|---|---|
| 01 | 24 1/7 | Post-invasive | Cordocentesis | 22q11.2 microdeletion | FISH |
| 02 | 28 4/7 | Post-invasive | Cordocentesis | 22q11.2 microdeletion | FISH |
| 03 | 22 5/7 | Post-invasive | Aminocentesis | 22q11.2 microdeletion | QF-PCR and FISH |
| 04 | 12 3/7 | Pre-invasive | Chorionic villus sampling | 22q11.2 microduplication (2.4Mb) | Array CGH |
| 05 | 20 2/7 | Pre-invasive | Amniocentesis | 22q11.2 microduplication (2.4Mb) | Array CGH |
| 06 | 21 4/7 | Pre-invasive | Amniocentesis | 3q29 microduplication (5.1Mb); 4q32.1-q35.2 microdeletion (32.9Mb) | Array CGH |

*FIG. 8*

NONINVASIVE PRENATAL MOLECULAR KARYOTYPING FROM MATERNAL PLASMA

CROSS-REFERENCES TO RELATED APPLICATIONS

This application is a continuation application of U.S. patent application Ser. No. 13/837,776, entitled "NONINVASIVE PRENATAL MOLECULAR KARYOTYPING FROM MATERNAL PLASMA," filed on Mar. 15, 2013, which claims priority from and is a non-provisional application of U.S. Provisional Patent Application No. 61/751, 213, entitled "Noninvasive Prenatal Molecular Karyotyping from Maternal Plasma," filed on Jan. 10, 2013, the entire contents of which are herein incorporated by reference for all purposes.

This application is related to commonly owned U.S. patent application Ser. No. 12/178,181 entitled "Diagnosing Fetal Chromosomal Aneuploidy Using Massively Parallel Genomic Sequencing" by Lo et al., filed Jul. 23, 2008, the disclosure of which is incorporated by reference in its entirety.

BACKGROUND

The presence of fetal DNA in maternal plasma has opened up exciting possibilities for noninvasive prenatal testing [1, 2]. Recently, there has been much interest in the use of massively parallel sequencing (MPS) for analyzing circulating fetal DNA for prenatal testing purposes. Thus, fetal trisomies 21, 13, 18 and selected sex chromosomal aneuploidies have been detected using MPS on maternal plasma DNA [3-7] and have been rapidly introduced into clinical service.

Apart from abnormalities due to copy number changes involving a whole chromosome, it would be important to evaluate whether the MPS-based analysis of maternal plasma might be sensitive enough for detecting subchromosomal deletions or duplications. In this regard, Peters et al reported the detection of a 4.2 Mb deletion on chromosome 12 in a maternal plasma sample obtained at the 35$^{th}$ week of gestation [8]. Jensen et al reported the detection of a 3 Mb deletion on chromosome 22 in maternal plasma samples obtained from two pregnant women at the 19$^{th}$ and 20$^{th}$ weeks of gestation [9]. Apart from the deleted region, Peters et al also performed statistical analysis on another region on chromosome 12, as well as 20 nonoverlapping 4 Mb regions on chromosome 14 [8]. Jensen et al, on the other hand, only focused their statistical analysis on the deleted region on chromosome 22 [9]. Thus, from the data presented by Peters et al and Jensen et al, it is not clear if the approach would be robust enough for a genomewide survey of microdeletions or microduplications, or indeed for the noninvasive determination of a fetal karyotype.

Lo et al reported that fetal single nucleotide polymorphisms (SNPs) can be genotyped in a genomewide scale using maternal plasma DNA sequencing [10]. In particular, these investigators have demonstrated that SNP alleles and mutations for single gene disorders that are inherited by a fetus from its mother can be elucidated by a process called relative haplotype dosage analysis [10]. Fan et al confirmed the robustness of relative haplotype dosage analysis and used this approach to detect a ~2.85 Mb deletion inherited by a fetus from its mother [11]. There are two concerns for using this method for the clinical implementation of noninvasive prenatal karyotyping. First, this method requires maternal haplotyping to be performed which would require additional analytical steps [12,13] or pedigree analysis. Second, it is unclear if this method could be used to detect de novo subchromosomal deletion or duplication.

BRIEF SUMMARY

Disclosed herein are methods, systems, and apparatus for detecting microamplifications or microdeletions in the genome of a fetus. In some embodiments, the method comprises receiving sequence tags for each of a plurality of DNA fragments in a biological sample; determining genomic positions for the sequence tags; determining whether the density of DNA in each of a plurality of genomic regions is aberrantly high or low; identifying as a microamplification a set of consecutive genomic regions having aberrantly high density; and identifying as a microdeletion a set of consecutive genomic regions having aberrantly low density. The biological sample may be a blood sample obtained noninvasively from a female subject pregnant with the fetus.

BRIEF DESCRIPTION OF THE DRAWINGS

FIGS. 3A-D and 4A-C show copy number aberrations detected in maternal plasma. The chromosome(s) showing copy number aberrations for each case is shown. The genomic position is shown on the x-axis and the z-score is plotted on the y-axis. Each vertical bar represents a 1-Mb bin. Regions with three or more consecutive 1-Mb bins of increased or reduced representation in plasma are indicated by green and red bars, respectively.

FIG. 5 is a table showing the fetal DNA percentage estimated by the alterations of the genomic representation of the regions affected by microdeletion/microduplication, and the proportions of chromosome Y sequences in the maternal plasma. (a) The chr Y approach is only applicable for those cases with a male fetus. (b) For case 05, as the mother also carried the aberration, the genomic representation of the affected region in the maternal plasma could not be used to determine the fetal DNA percentage. (c) The former and latter figures represent the fetal DNA percentage estimated from the microduplication on chromosome 3 and the microdeletion on chromosome 4, respectively.

FIG. 7 is a table showing the number of molecules required to be sequenced and aligned to achieve different diagnostic resolutions and diagnostic sensitivities assuming that the fetal DNA percentage is 5%. In this theoretical analysis, the diagnostic specificity is >99.9% for all cases based on the criteria that three consecutive bins having genomic representations >3 SD (for either over- or under-representation) from the mean of the references in the same direction.

FIG. 8 is a table showing information about the samples discussed in the Example.

DETAILED DESCRIPTION

Embodiments of this invention provide methods, systems, and apparatus for determining whether a microamplification or microdeletion exists in a fetal genome. In brief, this determination may be done by obtaining a biological sample and quantitating the amount of genomic DNA in the sample that originates from each of a plurality of genomic regions. The amount for each genomic region can be appropriately normalized to obtain a density for that region (i.e. a respective density), and compared with a reference density. A statistically significant difference between a respective density and reference density may indicate the presence of a microamplification or microdeletion within the genomic region, or spanning multiple genomic regions. To avoid false positives, a microamplification or microdeletion is identified when such a statistically significant difference exists for each of at least two consecutive genomic regions.

I. Introduction

Embodiments may be used to detect differences in copy number of genes or regions of chromosomes. Aberrantly high copy numbers of genes resulting from microamplification (also called microduplication) may cause overexpression or pathological expression of these genes, leading to diseases such as cancer. Conversely, low copy numbers of genes resulting from microdeletion may cause reduced expression or loss of biological (e.g. enzymatic) function. Therefore, detection of aberrant copy numbers can provide early warning of diseases the fetus may face before or after birth.

The biological sample may be obtained noninvasively from a female subject pregnant with the fetus. The sample may comprise blood, plasma, serum, urine, or saliva. Blood contains cell-free DNA fragments, and in a pregnant subject, a portion of these fragments are of fetal origin. The DNA fragments may be sequenced, such as by using massively parallel sequencing techniques, to obtain sequence tags. Any massively parallel sequencing platform may be used, including a sequencing-by-synthesis platform (e.g. Illumina/Solexa), a sequencing-by-ligation platform (e.g. the Life Technology SOLiD platform), or a single-molecule sequencing platform (e.g. Helicos or Pacific Biosciences). Each sequence tag contains all or part of the sequence of the DNA fragment from which it was generated, and can be aligned with a reference genome sequence to determine the genomic region of origin for the fragment.

Genomic regions, also referred to as 'bins', may be delineated by dividing up a reference genome sequence. The regions correspond to consecutive sequence portions of chromosomes. In preferred embodiments, each region is associated with one chromosome, and does not span multiple chromosomes. In some embodiments, the regions are of equal size, such as 1 Mb. The size of the genomic regions determines the resolution of the method disclosed herein, and the number of DNA fragments needed to identify microamplifications and microdeletions with statistical certainty.

II. Method

Figure 1:
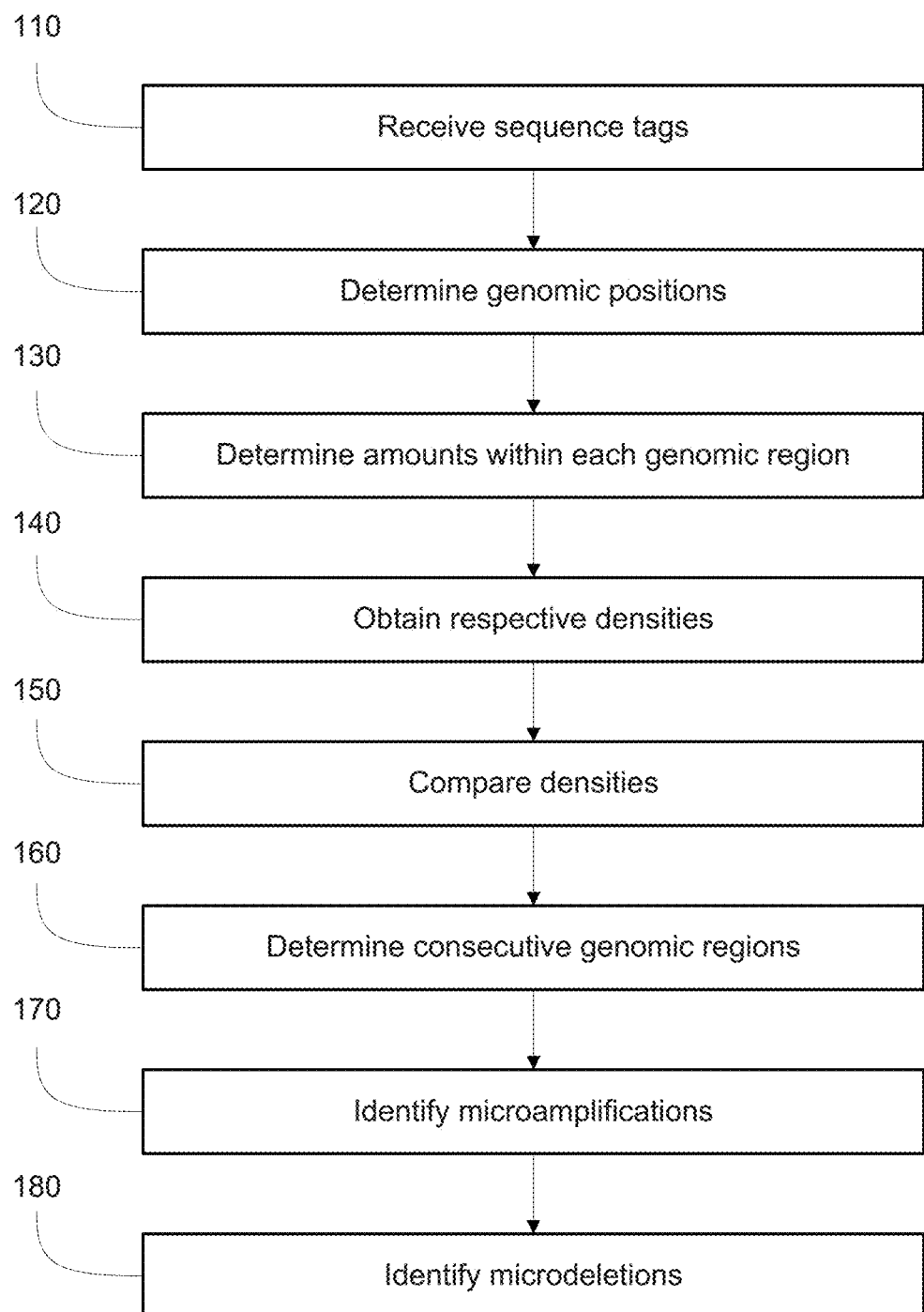
FIG. 1 is a flowchart showing a method of identifying microamplifications or microdeletions in a genome of a fetus.

FIG. 1 is a flowchart of a method 100 of identifying microamplifications or microdeletions in a genome of a fetus by analyzing a biological sample obtained from a female subject pregnant with the fetus, the biological sample including cell-free DNA from the fetus and from the female subject.

In step 110, one or more sequence tags for each of a plurality of DNA fragments in the biological sample are received. The sequence tags may be obtained by sequencing the DNA fragments using any method known in the art, for example Sanger sequencing or massively parallel sequencing. Each tag may be called a sequencing 'read', and may correspond to all of part of the DNA fragment from which it is generated. For example, the tag may contain the sequence of one end of the fragment or the interior of the fragment.

The DNA fragments may be isolated from the biological sample and prepared for sequencing using any known method. For example, the fragments may be copied before sequencing, such as using polymerase chain reaction (PCR), or may be ligated to adaptor molecules or 'barcode' sequences appropriate for the sequencing technology being used. The fragments may also be used to generate clonal clusters for bridge amplification, as is done in Illumina sequencing and similar technologies. The set of DNA fragments prepared for sequencing may be referred to as a 'sequencing library'.

In some embodiments, the sequence tags are generated according to paired-end sequencing, in which copies of a DNA fragment are sequenced in two directions, from opposite ends. Comparison of the sequencing data from the two directions allows verification of the sequence of the fragment, in particular at the ends of the fragment. The raw number of sequence tags obtained from paired-end sequencing provides an estimate of the number of DNA fragments in the sample. This number may vary between 1 million, 10 million, 100 million, 1 billion, and 10 billion, depending on the size and nature of the sample. In some embodiments, when multiple sequence tags represent an identical sequence (i.e. a sequence that is the same at both ends), duplicative tags may be discarded or excluded from further analysis.

In step 120, genomic positions for the sequence tags are determined. This is done by first aligning each sequence tag with a reference sequence, such as the non-repeat masked human reference genome (NCBI Build 36.1/hg18), using standard methods known in the art. In some embodiments, only tags with both ends aligned to the same chromosome are kept for further analysis. Tags may also be discarded if, for example, too many mismatches with the reference sequence exist, or if tags are not within a prescribed size range. Based on its sequence, each tag is then assigned to a genomic region or 'bin' within the reference sequence, as described above.

In step 130, for each of a plurality of genomic regions, the respective amount of DNA fragments within the genomic region is determined from sequence tags having genomic positions within the genomic region. The respective amount of DNA fragments for a genomic region is a parameter that may be calculated from the totality of data, or a portion thereof, contained in the sequence tags assigned to the region. These data include the number and lengths of tags and the amount of overlap between them, for example. The amount parameter is calculated with knowledge of the technique used to produce the sequence tags, and accounts for artifacts of this technique, such as the presence of multiple tags that may have originated from the same DNA fragment. The respective amount within a genomic region may be, for example, the number of fragments inferred to have existed in the sample and originating from the genomic region, or the total mass of DNA from the genomic region. In preferred embodiments, the respective amount of DNA fragments within a genomic region is a quantitative measure of the amount of DNA from that region in the sample.

In step 140, for each of a plurality of genomic regions, the respective amount is normalized to obtain a respective density. The normalization can be performed in many ways, for example by dividing the respective amount for a genomic region by the sum of respective amounts for the chromosome in which the genomic region occurs, or by the sum of respective amounts for the entire genome. The output of the normalization, the respective density, allows respective amounts from different genomic regions, for example from different chromosomes or samples, to be compared. The respective density may have many different interpretations, such as the fraction of the number of DNA fragments in a sample that originates from a genomic region. In some embodiments, when respective amounts can be compared directly, no normalization is necessary, and the respective density can equal the respective amount.

In step 150, for each of a plurality of genomic regions, the respective density is compared to a reference density to identify whether the respective density is statistically different from the reference density. The reference density for a genomic region may be obtained using the some or all of the data from the sample. The reference density may equal, for example, the mean of the respective densities for a chromosome or for the entire genome. The reference density may also be calculated using data from other samples. For example, samples may be obtained from a plurality of female subjects, each pregnant with a fetus, and steps 110-140 may be performed on each sample in an identical manner. The reference density for a particular genomic region is thus the mean of the respective densities for that region from all of the samples, or a subset of the samples. In some embodiments, independent data may exist to demonstrate that a subset of the female subjects are each pregnant with a fetus lacking genomic microamplifications or microdeletions, and thus reference densities can be calculated to reflect an absence of microamplifications or microdeletions.

In view of the above, the reference density may be (depending on how it is calculated) the same for multiple or all genomic regions, or a different value for each genomic region.

Identifying whether the respective density is statistically different from the reference density (i.e., whether the difference is statistically significant) may require knowledge of the distribution of respective densities used to calculate the reference density. For example, if the reference density for one genomic region is the mean of a set of respective densities, then a standard deviation can be calculated for that set. Using one respective density for that genomic region (e.g. for the sample of interest), the reference density, and the standard deviation, a statistical test may be performed. Such a statistical test may be a Z-test or Student's t-test, and may provide a probability that the respective density is drawn from the same distribution as the reference values. The difference between the respective density and reference density may be deemed statistically significant if this probability falls below a threshold. Alternatively, the difference may be deemed statistically significant if the difference exceeds a cutoff, such as a certain multiple of the standard deviation.

Preferably, comparisons of respective densities and reference densities, and identifications of statistical differences between them, are made using the same criteria for all genomic regions. Care must be taken in this step to note, in the event that a statistical difference exists for a genomic region, whether the respective density is higher or lower than the reference density.

In addition to the mean and standard deviation, other parameters may be calculated for a set of respective densities to determine a reference density and determine whether the respective and reference densities differ. Without limitation, these parameters include the median, mode, percentile, variance, skew, kurtosis, and others. In addition to the Z-test and t-test, other statistical tests may be employed for these purposes, for example tests using the foregoing parameters as inputs.

In step 160, it is determined whether any of the genomic regions identified to have a respective density statistically different from the reference density are consecutive with other so identified genomic regions. This determination may be made with respect to a portion of a chromosome, an entire chromosome, multiple chromosomes, or the entire genome, as fits the interests of the practitioner. Here, genomic regions are consecutive if they correspond to successive portions of the reference genome sequence. In preferred embodiments, genomic regions may only be consecutive if they correspond to the same chromosome. Of interest here are mainly sets of consecutive genomic regions wherein the respective density is statistically different from the reference density for each region, and all of the differences are in the same direction. That is, within such a set, all respective densities are higher than the reference densities (i.e., statistically higher), or all are lower (i.e., statistically lower). An example of such a set of genomic regions would be three consecutive regions where, for all three regions, the reference density is statistically different and higher (i.e., statistically higher) than the reference density. Consecutive genomic regions with respective densities statistically higher or lower than reference densities are consistent with microamplifications or microdeletions, respectively. Larger numbers of consecutive genomic regions in a set are consistent with larger microamplifications or microdeletions.

In step 170, first consecutive genomic regions are identified as a microamplification when at least N first genomic regions identified to have respective densities statistically higher than the reference densities are consecutive, N being an integer equal to or greater than two.

In step 180, second genomic regions are identified as a microdeletion when at least N second genomic regions identified to have respective densities statistically lower than the reference densities are consecutive.

III. Determining Aberrant Regions

To detect genomic microamplifications and microdeletions using the present invention, a reference genome sequence is divided into genomic regions or 'bins'. Fragments of DNA from a sample are associated with each region according to sequence, and the density of DNA in each region is determined. Regions with unusually high or low densities are considered 'aberrant', and may correspond to microamplifications or microdeletions. The criteria and procedures for identifying aberrant genomic regions, and determining whether they correspond to microamplifications or microdeletions, are discussed below.

A. Bins and Amounts

The size of genomic regions used herein can be of various sizes, as desired by the practitioner and appropriate for the sequencing method used. Smaller regions allow greater resolution of aberrant densities, but require larger numbers of DNA fragments (and therefore larger samples) to identify aberrant densities with statistical certainty. Conversely, larger regions provide poorer resolution but require smaller numbers of DNA fragments. In preferred embodiments, equally sized genomic regions are used to allow comparison and normalization of densities across chromosomes and the genome. The genomic regions may have sizes on the order of 100 kb, 200 kb, 500 kb, 1 Mb, 2 Mb, 5 Mb, or 10 Mb, for example. In some embodiments, the genomic regions are non-overlapping and/or contiguous (as discussed below), although in some cases there may be overlaps or gaps between regions, for example to simplify analysis of sequence tags occurring near the edges of regions.

DNA fragments may be sequenced using massively parallel sequencing techniques known in the art. In some embodiments, sequencing is performed using the sequencing-by-synthesis method of Illumina. This method is known to produce sequence tags with inconsistent efficiency depending on the GC content of the DNA fragment being sequenced. Accordingly, it may be desirable to correct the respective amounts of DNA determined for the genomic regions, which have variable levels of GC content on scales ranging from hundreds to thousands of base-pairs, to account for this sequencing artifact. When using 1 Mb genomic regions, each chromosome may first be divided into 100-kb bins and locally weighted scatterplot smoothing (LOESS) may be performed to correct for GC-associated bias in the number of sequence tags [20]. The 100-kb bins may then be merged into 1-Mb genomic regions, so that GC-corrected densities can be used in all subsequent calculations.

In one embodiment, the density of DNA in a genomic region (e.g., 1 Mb bin) may be calculated as the genomic representation ($GR_{x-y}$), where x and y denote the start and end genomic coordinates of the region. The number of sequence reads (or tags) that originates from each region is $RC_{x-y}$, and $GR_{x-y}$ is calculated using this equation [20]:

$$GR_{x-y} = \frac{RC_{x-y}}{RC_{total}}$$

where $RC_{total}$ is the total read counts.

Dividing by $RC_{total}$ is one example of normalizing the respective amount of DNA within a genomic region to obtain the respective density. In other implementations of the method, no ratio is determined and the values of $RC_{x-y}$ are directly compared between genomic regions. This can be done when $RC_{total}$ is controlled to be the same across samples.

B. Comparison to Reference

As described above, the respective density in a genomic region can be compared with a reference density. The reference density may be obtained in several different ways, for example averaging respective densities over multiple genomic regions, or averaging respective densities for the same genomic region obtained from multiple samples. To determine whether the respective density in a genomic region is aberrant, a parameter is calculated using the respective density and reference density, and the parameter is then compared to a cutoff. Examples of the parameter include the difference between the two values, the absolute value of the difference, or the ratio. These values may be manipulated as appropriate, for example multiplied by a scalar, to obtain the parameter and allow a meaningful comparison with a cutoff.

C. Cutoffs

In some embodiments, whether the parameter calculated from the respective density and reference density exceeds a cutoff can indicate whether the respective density is aberrant (statistically different). The sign of the parameter may indicate whether the respective density is aberrantly high or low, suggestive (but not dispositive) of a microamplification or microdeletion, respectively. For example, if the parameter is the simple difference between the respective density and reference density, then aberrantly high and low respective densities correspond to positive and negative signs of the parameter, respectively. Accordingly, the cutoff may be positive or negative, and for the parameter to exceed the cutoff may be understood to mean that it exceeds a positive cutoff or falls below a negative cutoff. Similarly, if the parameter is a ratio, then it may exceed the cutoff if it is larger than a certain value or smaller than the reciprocal of that value. The cutoff may be chosen in any way desired by the practitioner. For example, it may be arbitrary, or may be chosen to ensure that the determination of aberrant density is made with a desired level of statistical certainty.

In one embodiment, the parameter is compared to the cutoff in a z-test. A z-test is a statistical test and produces a z-score, which is a measure of how far a number is from the mean of a distribution, in terms of the width of the distribution. Here, the parameter used to compare the respective density and reference density is the difference between these densities divided by the standard deviation of the values used to calculate the reference density.

By way of demonstration, biological samples were obtained from eight pregnant (singleton) female subjects with normal fetal karyotypes, and respective densities were calculated for individual 1 Mb genomic regions using each sample. For a given genomic region x-y, the respective densities from the samples were averaged (i.e. the mean was calculated) to obtain a reference density $meanGR_{x-y-reference}$, and the standard deviation of the respective densities, $SD_{x-y-reference}$ was calculated. A test sample was then obtained from another pregnant female subject of interest, and the respective density for the region x-y ($GR_{x-y-test}$) was calculated using data from the test sample. The z-score for this respective density, z-score$_{GRx-y}$, was calculated as follows:

$$z\text{-score}_{GR_{x-y}} = \frac{GR_{x-y_{test}} - meanGR_{x-y_{reference}}}{SD_{x-y_{reference}}}$$

The z-score was then compared to a cutoff, for example 3. Z-scores greater than +3 or smaller than −3 indicated that respective density from the test sample was aberrantly high or low, respectively. To minimize the systematic inter-sample variations between different chromosomes, a median correction was performed for each chromosome. Thus, the median genomic representation of all the genomic regions corresponding to a particular chromosome was used as a baseline. For all regions located on that particular chromosome, the difference from this baseline value was used for the calculation of the z-score.

The z-score, or any other measure of aberrant density in a genomic region, may be sensitive to the abundance of fetal DNA in the sample. As is known in the art, a significant percentage of the cell-free DNA in a blood sample of a pregnant woman is fetal in origin. This percentage has been observed to range from less than 1% to over 20%, depending on the time of gestation and other factors. In the method described herein, sequence tags are generated from both maternal and fetal DNA in the sample. If a microamplification or microdeletion is present in the genome of the fetus but not the mother, a relatively small aberration is observed in the density of DNA in the corresponding genomic region(s) because the minority of the DNA used to generate sequence tags and determine the density is fetal. Conversely, if the microamplification or microdeletion is maternal in origin (i.e. maternally inherited), it is present in the genomes of both the fetus and mother, and therefore in substantially all of the DNA in the sample. Thus, a higher aberration in the density of DNA will be observed. (A microamplification or microdeletion is unlikely to be present in the maternal genome but not the fetal genome).

Accordingly, a second cutoff may be used to determine whether an aberration in the respective density of DNA in a genomic region is maternally inherited. The second cutoff is typically larger than the cutoff used to identify an aberration in the fetal genome, and requires a larger or more statistically significant departure of the respective density from the reference density. When the respective density and reference density are compared using a z-test, for example, the z-score that serves as the cutoff for identifying an maternally inherited aberration may be several times that used to identify an aberration absent from maternal genome. In some embodiments, the second cutoff corresponds to a z-score of 10, 20, or more.

Higher aberrations in the density of DNA, such as those resulting from maternally inherited microamplifications or microdeletions, require less DNA and fewer sequence tags to identify with the same level of certainty than lower aberrations. Accordingly, the sensitivity of the methods disclosed herein to detect fetal genomic abnormalities depends on the percentage of fetal DNA in the sample (fetal %), as is discussed below. The extent of under- or overrepresentation of sequence tags in an aberrant genomic region is linearly correlated with the fetal DNA percentage for that region [4]. In some embodiments, the fetal DNA percentage is calculated using the following equation:

$$\text{Fetal \%} = \frac{\left(GR_{x-y_{test}} - meanGR_{x-y_{reference}}\right) \times 2}{meanGR_{x-y_{reference}}} \times 100\%$$

D. Reference Density

As described above, the respective density of DNA in a particular genomic region is compared with a reference density to determine whether the respective density is aberrant. The reference density may be calculated in many different ways using the data obtained from one sample or from multiple samples. In the case of one sample, the reference density can be, for example, the mean of respective densities for a set of genomic regions. This set may correspond to part or all of a chromosome, multiple chromosomes, or the entire genome. In the case of multiple samples, each sample is typically acquired from a different individual. The reference density for a genomic region may be the respective density for that region, or set of regions, averaged across individuals. In some embodiments, biological samples are obtained from pregnant female subjects with known normal fetal karyotypes in order to establish reference densities that reflect an absence of microamplifications or microdeletions. The reference densities may then be compared with respective densities for a test subject with an unknown fetal karyotype. In some embodiments, the fetal karyotypes of multiple (or all) individuals are unknown, and reference densities are calculated without prior knowledge of aberrations that may be present in the samples of these individuals.

The reference density can be the same or different for different genomic regions. For example, the same value may be used for all genomic regions on a chromosome or in the genome. Alternatively, a different value may be assigned to the reference density for each genomic region. The reference density need not be calculated from respective densities, such as by averaging respective densities—for example, it can simply reflect the relative sizes of the genomic regions. As described above, the reference density may be corrected for artifacts, such as non-uniform generation of sequence tags for different chromosomes or genomic regions.

E. Avoiding False Positives

After the respective density for a genomic region has been found to be aberrant (e.g., statically higher or lower than the reference density), a microamplification or microdeletion may be identified if the genomic region is consecutive with at least one other genomic region that is also aberrant. As discussed above, for such an identification to be made, the respective density must depart from the reference density in the same direction for the consecutive regions. Thus, a microamplification corresponds to consecutive genomic regions where the respective density is aberrantly high in each region, and a microdeletion corresponds to consecutive genomic regions where the respective density is aberrantly low.

Depending on the method used to compare the respective density with the reference density for a genomic region, there may be a significant probability that the region will have an aberrant density of DNA when in fact no microamplification or microdeletion is present. When many genomic regions are established and their respective densities are evaluated, therefore, some regions may be deemed aberrant simply by chance. Requiring consecutive aberrant regions to identify microamplifications or microdeletions reduces the probability of false positives, i.e. identifying such events in error. This requirement also sets the resolution limit of the method at a multiple (e.g. 2 or 3) of the size of the genomic regions. For example, the resolution limit for 1 Mb genomic regions is 2 Mb if two or more consecutive regions are required to identify a microamplification or microdeletion.

Microamplifications or microdeletions identified using the method described herein may be verified using other methods known in the art. Such other methods include amniocentesis and cordocentesis, for example, and may be invasive or include a risk of miscarriage. Verification of aberrant copy numbers using multiple methods may further reduce the likelihood of false positives.

Herein, two or more genomic regions are considered consecutive if they occupy consecutive sequence positions along a chromosome, or in a genomic reference sequence, with no other genomic regions between or among them. In some embodiments, pairs of consecutive regions adjoin each other directly in sequence, and are therefore considered contiguous. A sequence gap between two regions (for example, a few base-pairs) precludes the regions from being contiguous, but does not preclude them from being consecutive, if the gap is not treated as another genomic region under the methods disclosed herein. In some embodiments, genomic regions are non-overlapping, but overlapping regions may be used instead and can be consecutive. The practitioner may wish to establish genomic regions that are not contiguous, or that are overlapping, to focus on certain regions of the genome, to simplify data analysis, or for other reasons.

IV. Simulation Analyses

The sensitivity and specificity of detecting a microdeletion or a microduplication may be affected by different parameters including the fetal % in the sample, the number of plasma DNA molecules sequenced and aligned, and the size of the aberration. Therefore, computer simulation analyses may be performed to determine 1) the sensitivity of detecting a microdeletion/microduplication (for example, ~3 Mb in size) with the existing sequencing depth; and 2) the number of molecules needed to be analyzed to achieve a particular sensitivity (e.g. 95%/99%) at a particular fetal % (e.g. 5%).

In each simulation analysis, the whole genome (3,000 Mb) may be divided into bins of equal size according to the desired resolution, for example 3 Mb. In some embodiments, for the detection of a subchromosomal aberration, three consecutive bins are required to have genomic representation of >3 standard deviations (either over- or under-representation) away from the mean of the reference group in the same direction. Therefore, the bin size would be equal to ⅓ of the desired diagnostic resolution. For example, a bin size of 1 Mb is needed to detect aberrations of 3 Mb. It may be assumed that the three bins covered by the microdeletion/microduplication have an abnormal genomic representation resulting from the contribution of the minority population of fetal DNA. In the plasma, the expected proportion of total molecules (E) falling into a bin within an affected region can be calculated as:

$$E = \left(1 + \frac{f}{2} \times d\right) \times \frac{1}{T}$$

where f is the fetal DNA percentage in plasma, d is the change in the chromosome number in the aberration (d equals to −1 for microdeletion and +1 for microduplication), and T is the total number of bins for the whole genome Simulations, for example of 1,000 normal cases and 1,000 affected cases, may be performed assuming a binomial distribution of the plasma DNA molecules with the expected plasma representations as calculated above. The fetal %, the bin size and the total number of molecules being analyzed may be changed to achieve the desired purpose. The simulation may be conducted using the rbinom function in R (www.r-project.org/).

V. Example

This Example provides for identifying microamplifications and microdeletions in human fetal and maternal DNA.

A. Framework for Data Analysis

One lane of a flow cell on an Illumina HiSeq 2000 sequencer was used to analyze each maternal plasma sample of the six test cases and the eight controls. A mean of 211 million (range: 177 million to 236 million) DNA fragments were sequenced from each plasma DNA sample. Such sequencing resulted in a mean of 144 million (range: 96 million to 180 million) alignable and non-duplicated sequenced reads per case which was equivalent to 4.81 folds of the haploid human genome.

To obtain a plasma karyotype, the entire genome was divided into 2,687 1-Mb bins. The genomic representation for each 1-Mb bin of the test sample was compared with that of the reference group. For regions with normal genomic representation, the expected distributions of z-scores of all 1-Mb bins would be close to zero. A reference interval was defined as a z-score from +3 to −3. With such a reference interval, statistically approximately 0.3% of the bins would fall outside of this interval just by chance. As 2,687 bins were analyzed, one would on average expect that 8 bins would fall outside of the reference interval just by chance. To reduce false-positive calls, an additional criterion was therefore included of calling a copy number aberration only if three consecutive 1-Mb bins exhibited a z-score outside of the reference interval and in the same direction.

B. Detection of Subchromosomal Copy Number Aberrations

Figure 2:
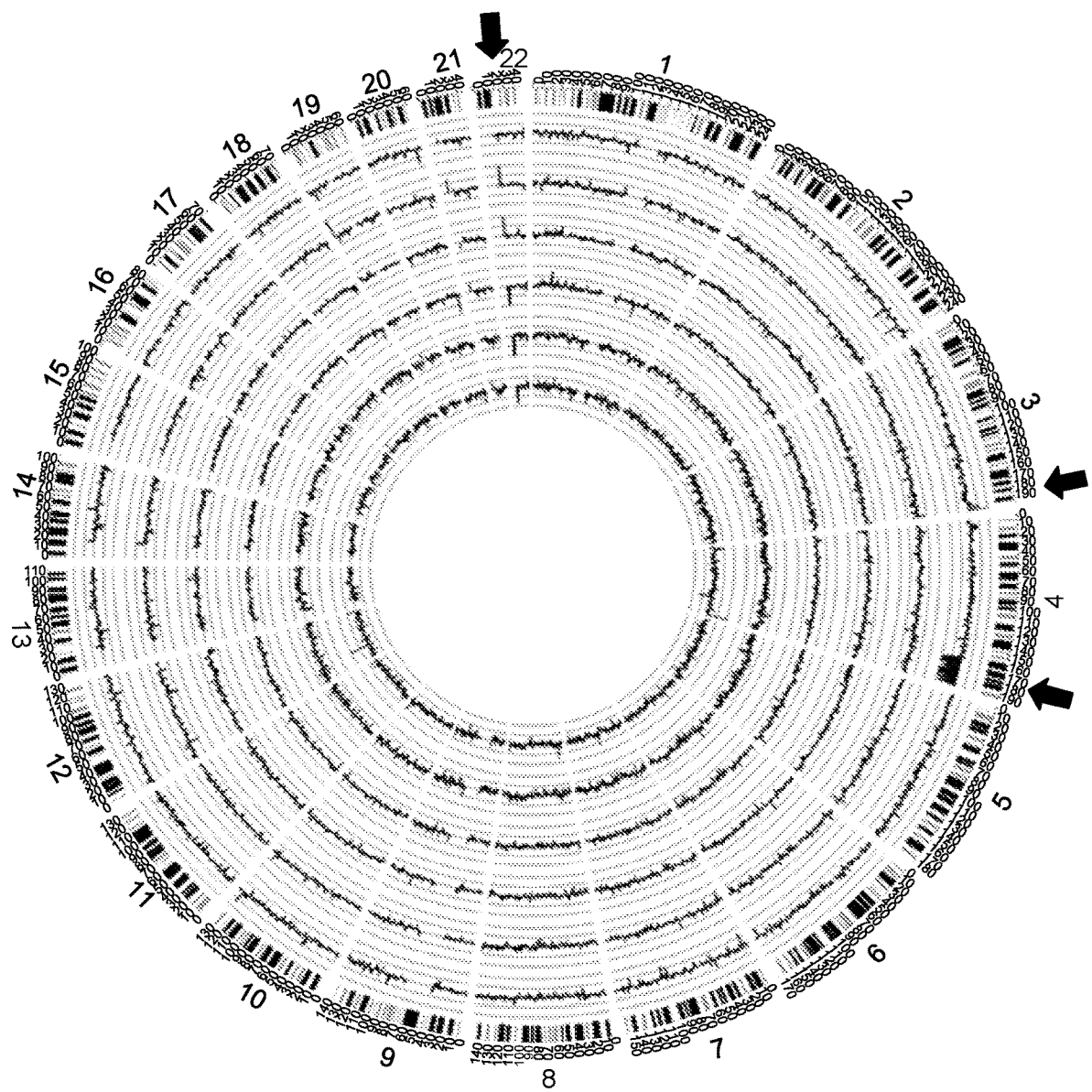
FIG. 2 is a Circos plot of the detected copy number aberrations across the genome in maternal plasma. From inside to outside: cases 01 to 06. Chromosome ideograms (outermost ring) are oriented pter to qter in a clockwise direction. Each bar represents a 1-Mb window. Regions with three or more consecutive 1-Mb bins of increased or reduced representation in plasma are indicated by green and red bars, respectively. Red arrows highlight the approximate chromosomal locations on these aberrant regions.
Figure 4A:
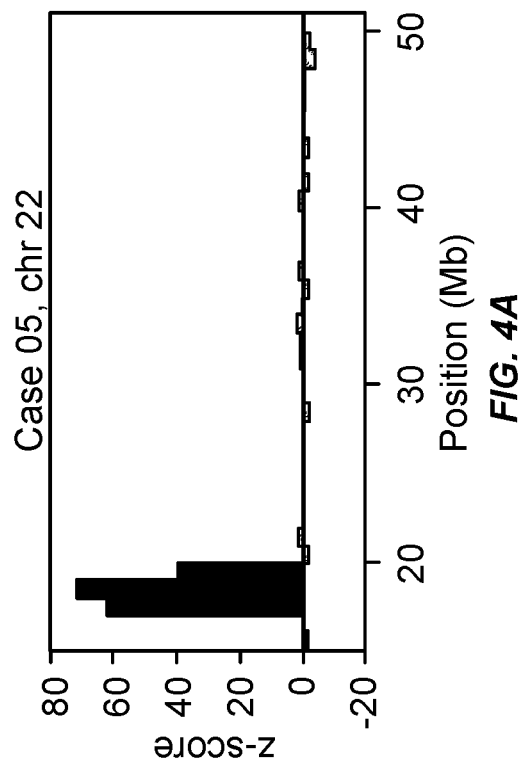
Figure 4B:
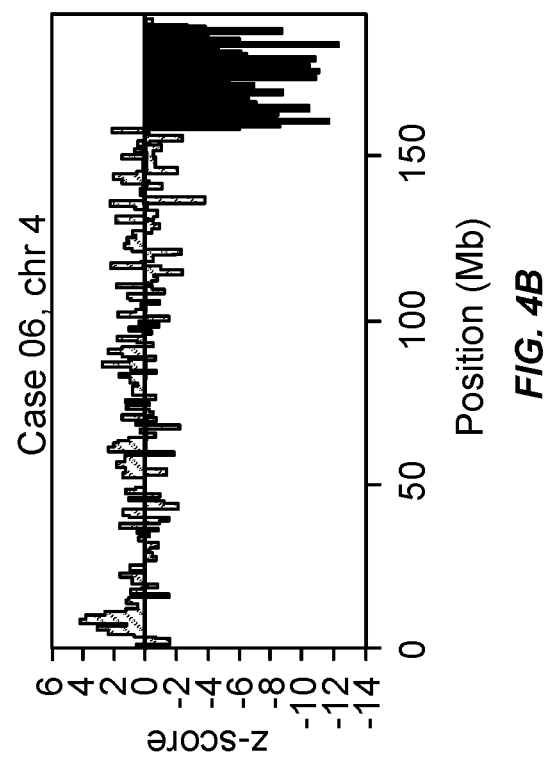
Figure 4C:
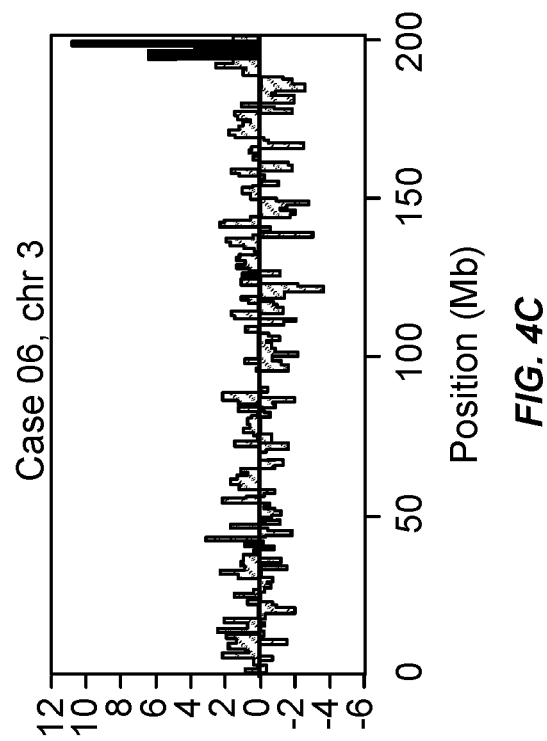

The z-scores of all 1-Mb bins across the entire genome for each case were plotted using Circos plots [21] (FIG. 2). In the test samples, 94.9%-98.7% of the 1-Mb bins showed normal representation. With the above-mentioned criterion of calling a copy number aberration only if three consecutive bins showed the same aberration, the copy number aberrations were correctly identified in all cases with no false-positives.

FIGS. 3A-D and 4A-C show the z-scores of all 1-Mb bins of the chromosome(s) showing copy number aberrations for each case. For cases 01, 02 and 03, underrepresentation was detected in three consecutive 1-Mb bins on the q arm of chromosome 22. These were the three cases with de novo 22q11.2 microdeletion. For cases 04 and 05, overrepresentation was detected in three consecutive 1-Mb bins on chromosome 22q. Case 04 was a case with a de novo 22q11.2 microduplication of 2.4 Mb. Case 05 was a case with a maternally-inherited microduplication in the same region. For case 05, since the mother herself harbored the microduplication, the aberration could easily be detected in the maternal plasma. This was supported by the extremely high z-score values (range, 39.7 to 71.7) for the three consecutive bins. Further exploration of noninvasive prenatal testing of the fetus could proceed with the use of SNP-based methods, namely relative mutation dosage or relative haplotype dosage analysis [10,11, 22]. For case 06, five consecutive 1-Mb bins were detected with overrepresentation on the q arm of chromosome 3 and thirty-one consecutive 1-Mb bins were detected with underrepresentation on the q arm of chromosome 4, which corresponded to a 5-Mb duplication on 3q and a 31-Mb deletion on 4q. For all cases, the copy number aberrations detected had sizes comparable to those confirmed by array CGH, FISH and/or QF-PCR. For case 05, the microduplication carried by the mother was confirmed by array CGH. For case 06, the balanced translocation carried by the mother was confirmed by full karyotyping.

C. Fetal DNA Percentage

DNA sequences from the regions showing under- or overrepresentation were used to estimate the fetal % in maternal plasma (FIG. 5). This approach was validated by comparing the fetal % calculated using this method and that using the chr Y-based method [4] for the three cases carrying male fetuses (i.e., cases 02, 03 and 04). The fetal % values agreed well between the two methods (FIG. 5). For the five cases with fetal de novo copy number aberrations, the fetal % ranged from 9.2% to 17.8%. For case 05, the fetal % estimated by the genomic representation of the microduplication was 96.7%, suggesting that almost all of the circulating DNA would harbor this change. This result is consistent with the fact that the mother carried the aberration.

D. Simulation Analysis for Diagnostic Sensitivity

Figure 6:
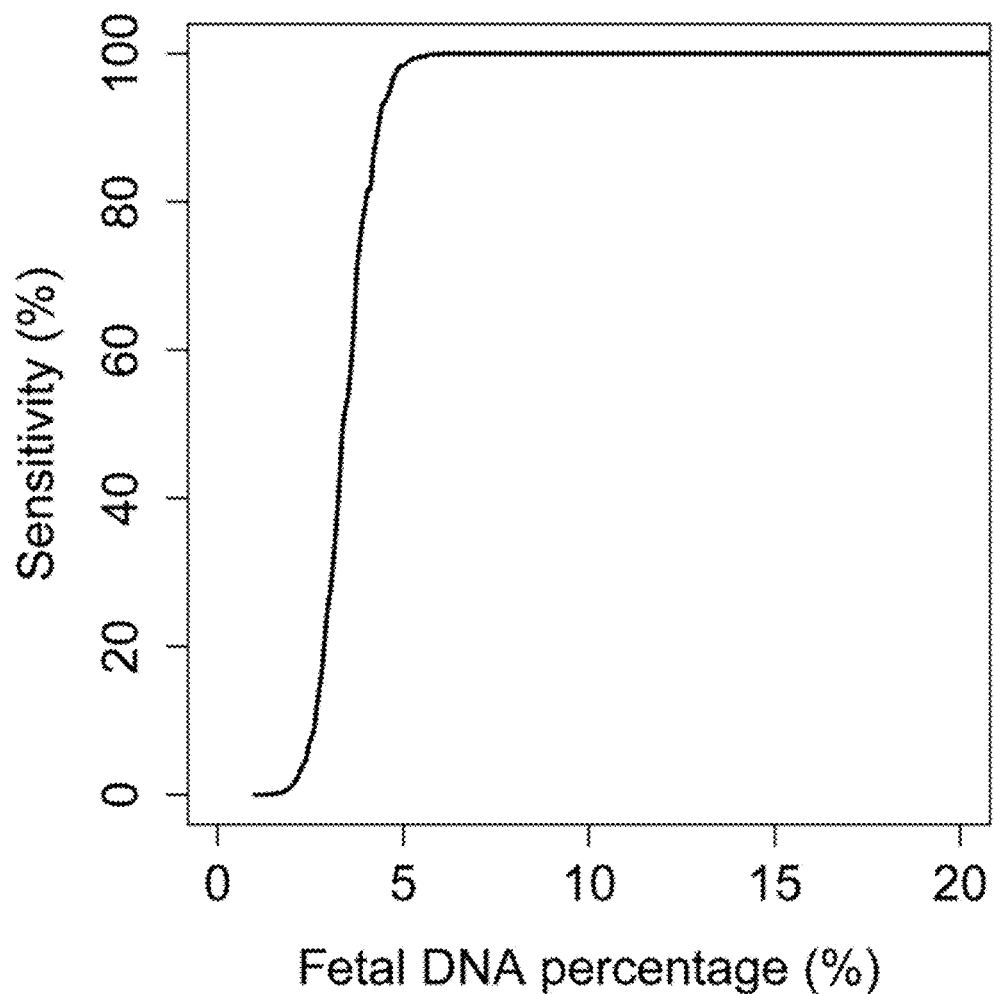
FIG. 6 shows diagnostic sensitivity for the detection of a 3 Mb microdeletion/microduplication. The diagnostic sensitivity for detecting the aberration is plotted against the fetal DNA percentage. The computer simulation analysis was performed assuming that a total of 150 million plasma DNA molecules were analyzed.

Computer simulations were used to determine the diagnostic sensitivity of shotgun MPS-based noninvasive prenatal molecular karyotyping (FIG. 6). With the existing sequencing depth of ~150 million reads, the diagnostic sensitivity for detecting a 3 Mb chromosomal aberration would be approximately 96% when the fetal % is 5%. The sensitivity would increase to 99% when the fetal % reaches 6%. To detect chromosomal aberrations of smaller sizes, more plasma DNA molecules would need to be analyzed. FIG. 7 shows the number of plasma DNA molecules that needs to be analyzed to achieve 3 Mb, 2 Mb and 1 Mb diagnostic resolution with 95%/99% sensitivity, using the three consecutive bins criterion. To achieve a 95% diagnostic sensitivity, approximately 42,000 molecules in each bin would need to be analyzed. Thus, the total number of plasma DNA molecules that needs to be analyzed to detect a 2 Mb and a 1 Mb microdeletion/microduplication for a 95% diagnostic sensitivity would be 192 million and 380 million, respectively. To achieve a 99% diagnostic sensitivity, the total number of molecules that needs to be analyzed would be 240 million and 480 million for the two different resolutions, respectively.

E. Discussion

In this work, the feasibility of performing the noninvasive prenatal detection of fetal chromosomal microdeletions and microduplications was demonstrated on a genomewide level and at 3-Mb resolution. Fetus-derived subchromosomal deletions or duplications involving chromosomes 3q, 4q or 22q in 5 cases were detected. In the sixth case, maternally-derived microduplication of chromosome 22q was detected, as evidenced by the very high z-scores seen. Indeed, cases 04 and 06 represent the first time that a fetal microduplication has been detected noninvasively from maternal plasma. These results represent an important step forward compared with the previous reports by Peters et al [8] and Jensen et al [9] which were focused primarily on testing for copy number aberrations in one or a small number of genomic regions. The data presented herein clearly demonstrate that shotgun MPS can be used for detecting subchromosomal copy number aberrations on the genomewide scale, in other words, for obtaining a fetal molecular karyotype.

In three of the studied cases, maternal plasma samples were taken after invasive procedures. The fetal DNA percentages in these cases range from 9.2 to 17.4% which are within the range previously observed by Chiu et al [4] for samples collected prior to invasive procedures. Similarly, while most of the studied samples were taken beyond the 20$^{th}$ week of gestation, the fetal DNA percentages of these cases are also largely overlapping with those of samples taken earlier in gestation. Nonetheless, it would be useful to validate these results in future, prospective, large-scale multicenter studies using samples collected prior to any invasive procedures in the first and early second trimesters.

Analytically, the diagnostic algorithm requires, in some embodiments, three consecutive bins with z-scores of all above +3 or all below −3 for detecting a subchromosomal copy number aberration. This algorithm requires a copy number aberration to be detectable over a contiguous stretch of approximately 3 Mb. Indeed, as indicated by the data, the algorithm was able to detect a copy number aberration of 2.4 Mb (cases 04 and 05).

The depth of sequencing performed to reach such diagnostic resolution was much higher than that needed for trisomy testing. Thus, for each case, sequencing was performed in one lane of an Illumina HiSeq 2000 sequencer, compared with the 12-plex shotgun sequencing using the same sequencing platform that is performed by at least one commercial provider of trisomy testing. At the current depth of sequencing and its resultant diagnostic resolution of 3 Mb, the current protocol could cover approximately 20% of the known pathogenic copy number variants [23]. It was predicted above that 240 million and 480 million plasma DNA molecules would need to be sequenced and aligned to extend the diagnostic resolution to 2 Mb and 1 Mb, respectively, with a 99% sensitivity. At these diagnostic resolutions, shotgun MPS of maternal plasma DNA would be expected to cover approximately 50% and 80%, respectively, of the known pathogenic copy number variants [23]. With a continual increase in throughput of massively parallel sequencers and the concomitant reduction in sequencing costs, it is likely that the costs associated with such sequencing depths will reach a level that would be acceptable to healthcare providers in a few years' time. The amount of sequencing required by this approach is already a significant reduction over a previously reported fetus-derived single nucleotide variation detection method which was performed using billions of sequenced reads per sample [10]. Further reduction in costs could come from targeted sequencing of genomic regions harboring pathogenic copy number variants, similar to what has been achieved for fetus-derived single nucleotide variation detection from maternal plasma [24,25]. Finally, the advent of single molecule sequencing would also be expected to further improve the diagnostic accuracy of this approach as amplification process, which might distort the genomic representation of the sequenced molecules, is not needed [26].

In summary, it is demonstrated that it is feasible to obtain a noninvasive prenatal molecular karyotype by shotgun MPS of maternal plasma DNA. This method can detect fetal de novo copy number changes, unbalanced translocations and maternal copy number changes. These results have further expanded the diagnostic spectrum of noninvasive prenatal diagnosis. In conclusion, methods based on MPS analysis of maternal plasma DNA have been developed for the prenatal detection of whole chromosome aneuploidies [3-7], subchromosomal copy number changes and fetal mutations for single gene disorders [10]. This array of noninvasive tests could in the first instance be applied for screening of fetal genomic and chromosomal abnormalities. Abnormalities revealed by the noninvasive maternal plasma DNA tests could be further confirmed by conventional invasive prenatal testing. Upon validation by large-scale prospective studies, it is envisioned that noninvasive maternal plasma DNA sequencing could provide prenatal assessment of a large spectrum of fetal genomic and chromosomal abnormalities and provide safer prenatal assessments.

F. Materials and Methods

Ethical Statement.

The study was approved by the Joint Chinese University of Hong Kong—Hospital Authority New Territories East Cluster Clinical Research Ethics Committee. Pregnant women were recruited with written informed consent from the Prince of Wales Hospital, the Kwong Wah Hospital and the Tsan Yuk Hospital in Hong Kong, and the Asan Medical Center in Seoul.

Sample Collection.

For cases 01, 02, and 03, maternal peripheral blood samples were collected into EDTA-containing tubes after invasive procedures (Table 1). For cases 04, 05 and 06, maternal peripheral blood samples were collected before performing any invasive procedures. Maternal blood samples were drawn at 12 3/7 to 28 4/7 weeks of gestation (FIG. 8).

Among the six test samples, there were three cases (cases 01, 02 and 03) of fetal de novo 22q11.2 microdeletion, one case (case 04) of fetal de novo 22q11.2 microduplication (2.4 Mb) and one case (case 05) of maternally-inherited 22q11.2 microduplication (2.4 Mb). There was also one case (case 06) in which the mother had a balanced translocation of t(3,4)(q29;q32) and the fetus was found to have 3q29 microduplication (5.1 Mb) and 4q32.1-q35.2 deletion (32.9 Mb). Full karyotyping was performed and the fetal karyotypes were further ascertained by array comparative genomic hybridization (array CGH) [16], fluorescence in situ hybridization (FISH) or a combination of quantitative fluorescence PCR (QF-PCR) and FISH.

Sample Processing and DNA Extraction.

Peripheral blood samples were centrifuged at 1600 g for 10 min at 4° C. and the plasma portion was recentrifuged at 16000 g for 10 min at 4° C. [17]. Cell-free DNA was extracted from 1.8 to 8.4 mL of maternal plasma with the QIAamp DSP DNA Blood Mini Kit (Qiagen) as described previously [3]. The extracted plasma DNA was quantified by a real-time PCR assay targeting the leptin (LEP) gene as described previously [18].

Plasma DNA Sequencing.

Sequencing libraries of plasma DNA were prepared with the Paired-End Sequencing Sample Preparation Kit (Illumina) as described previously [19]. 13 to 20 ng of the extracted plasma DNA was used for library preparation. The adaptor-ligated plasma DNA was enriched by a 12-cycle PCR. Cluster generation was performed on a cBot clonal amplification system (Illumina) with the TruSeq PE Cluster Generation Kit v3 (Illumina). Each library (both test and reference samples) was sequenced with one lane of a flow cell on a HiSeq 2000 sequencing system (Illumina) in a paired-end format of 50-bp×2.

Sequence Alignment and Filtering.

Paired-end reads were aligned to the non-repeat masked human reference genome (NCBI Build 36.1/hg18) using the Short Oligonucleotide Alignment Program 2 (SOAP2) (http://http://soap.genomics.org.cn/). Up to two nucleotide mismatches were allowed for each member of the paired-end reads. Only paired-end reads with both ends aligned to the same chromosome with the correct orientation, spanning an insert size <600 bp were included in downstream analysis. Duplicated reads which were defined as paired-end reads showing identical start and end positions in the human genome, were also removed.

G. Summary of Example

Fetal DNA is present in the plasma of pregnant women. Massively parallel sequencing of maternal plasma DNA has been used to detect fetal trisomies 21, 18, 13 and selected sex chromosomal aneuploidies noninvasively. Case reports describing the detection of fetal microdeletions from maternal plasma using massively parallel sequencing have been reported. However, these previous reports were either polymorphism-dependent or used statistical analyses which were confined to one or a small number of selected parts of the genome. In this Example, a procedure was reported for performing noninvasive prenatal karyotyping at 3 Mb resolution across the whole genome through the massively parallel sequencing of maternal plasma DNA. This method has been used to analyze the plasma obtained from 6 cases. In 5 cases, fetal microduplications or microdeletions have been detected successfully from maternal plasma. The two cases with fetal microduplications represented the first noninvasive prenatal detection of such changes from maternal plasma. In the remaining case, the plasma DNA sequencing result was consistent with the pregnant mother being a carrier of a microduplication. Simulation analyses were performed for determining the number of plasma DNA molecules that would need to be sequenced and aligned for enhancing the diagnostic resolution of noninvasive prenatal karyotyping to 2 Mb and 1 Mb. In conclusion, noninvasive prenatal molecular karyotyping from maternal plasma by massively parallel sequencing is feasible and would enhance the diagnostic spectrum of noninvasive prenatal testing.

VI. Computer System

Figure 9:
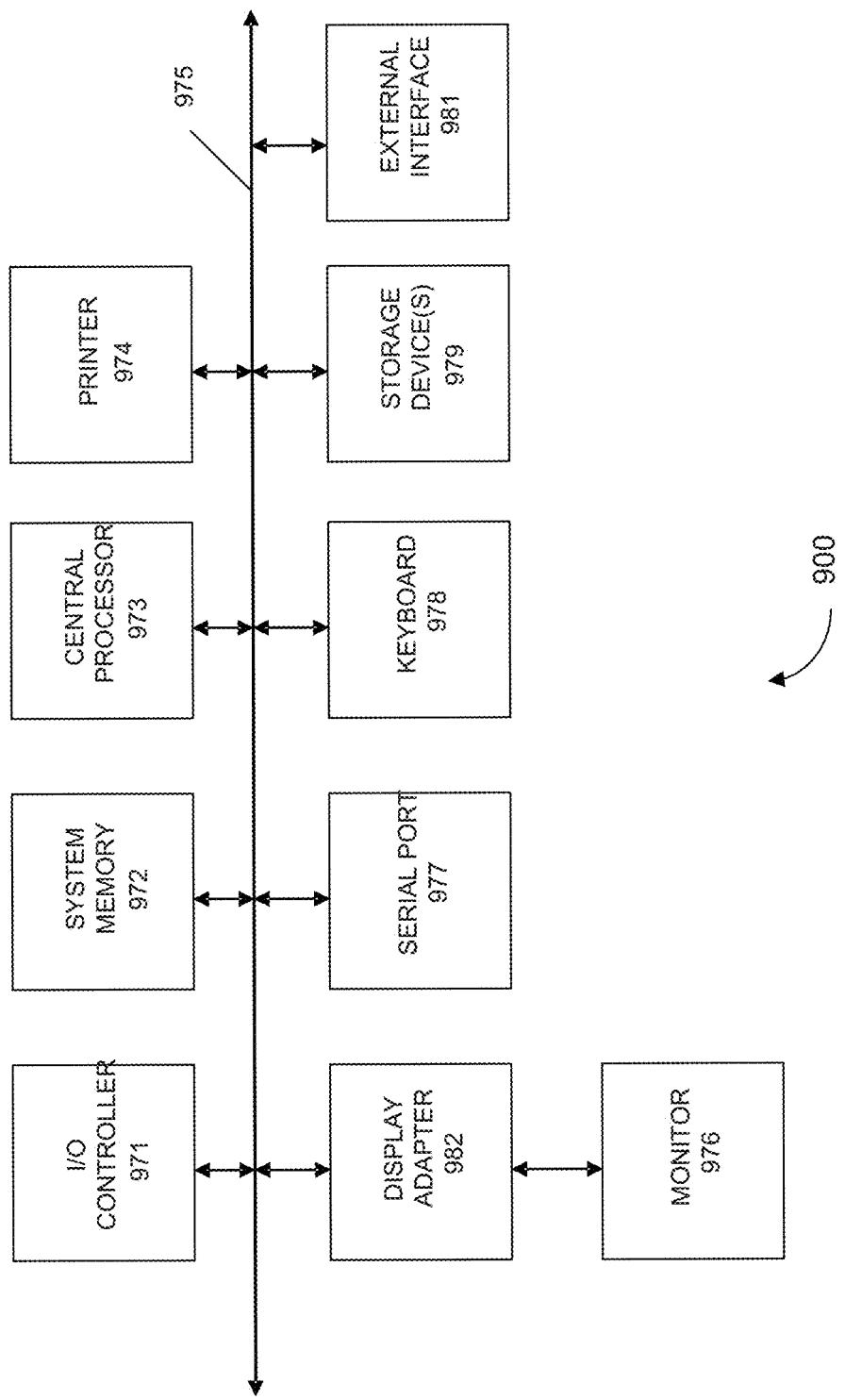
FIG. 9 shows a block diagram of an example computer system 900 usable with system and methods according to embodiments of the present invention.

Any of the computer systems mentioned herein may utilize any suitable number of subsystems. Examples of such subsystems are shown in FIG. 9 in computer apparatus 900. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 9 are interconnected via a system bus 975. Additional subsystems such as a printer 974, keyboard 978, storage device(s) 979, monitor 976, which is coupled to display adapter 982, and others are shown. Peripherals and input/output (I/O) devices, which couple to I/O controller 971, can be connected to the computer system by any number of means known in the art, such as serial port 977. For example, serial port 977 or external interface 981 (e.g. Ethernet, Wi-Fi, etc.) can be used to connect computer system 900 to a wide area network such as the Internet, a mouse input device, or a scanner. The interconnection via system bus 975 allows the central processor 973 to communicate with each subsystem and to control the execution of instructions from system memory 972 or the storage device(s) 979 (e.g., a fixed disk, such as a hard drive or optical disk), as well as the exchange of information between subsystems. The system memory 972 and/or the storage device(s) 979 may embody a computer readable medium. Any of the data mentioned herein can be output from one component to another component and can be output to the user.

A computer system can include a plurality of the same components or subsystems, e.g., connected together by external interface 981 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

REFERENCES

1. Lo Y M D, Corbetta N, Chamberlain P F, Rai V, Sargent I L, et al. (1997) Presence of fetal DNA in maternal plasma and serum. Lancet 350: 485-487.
2. Lo Y M D, Chiu R W K (2012) Genomic analysis of fetal nucleic acids in maternal blood. Annu Rev Genomics Hum Genet 13: 285-306.
3. Chiu R W K, Chan K C A, Gao Y, Lau V Y M, Zheng W, et al. (2008) Noninvasive prenatal diagnosis of fetal chromosomal aneuploidy by massively parallel genomic sequencing of DNA in maternal plasma. Proc Natl Acad Sci USA 105: 20458-20463.
4. Chiu R W K, Akolekar R, Zheng Y W L, Leung T Y, Sun H, et al. (2011) Non-invasive prenatal assessment of trisomy 21 by multiplexed maternal plasma DNA sequencing: large scale validity study. BMJ 342: c7401.
5. Palomaki G E, Kloza E M, Lambert-Messerlian G M, Haddow J E, Neveux L M, et al. (2011) DNA sequencing of maternal plasma to detect Down syndrome: An international clinical validation study. Genet Med 13: 913-920.
6. Palomaki G E, Deciu C, Kloza E M, Lambert-Messerlian G M, Haddow J E, et al. (2012) DNA sequencing of maternal plasma reliably identifies trisomy 18 and trisomy 13 as well as Down syndrome: an international collaborative study. Genet Med 14: 296-305.
7. Bianchi D W, Platt L D, Goldberg J D, Abuhamad A Z, Sehnert A J, et al. (2012) Genome-wide fetal aneuploidy detection by maternal plasma DNA sequencing. Obstet Gynecol 119: 890-901.
8. Peters D, Chu T, Yatsenko S A, Hendrix N, Hogge W A, et al. (2011) Noninvasive prenatal diagnosis of a fetal microdeletion syndrome. N Engl J Med 365: 1847-1848.
9. Jensen T J, Dzakula Z, Deciu C, van den Boom D, Ehrich M (2012) Detection of microdeletion 22q11.2 in a fetus by next-generation sequencing of maternal plasma. Clin Chem 58: 1148-1151.
10. Lo Y M D, Chan K C A, Sun H, Chen E Z, Jiang P, et al. (2010) Maternal plasma DNA sequencing reveals the genome-wide genetic and mutational profile of the fetus. Sci Transl Med 2: 61ra91.
11. Fan H C, Gu W, Wang J, Blumenfeld Y J, El-Sayed Y Y, et al. (2012) Non-invasive prenatal measurement of the fetal genome. Nature 487: 320-324.
12. Fan H C, Wang J, Potanina A, Quake S R (2011) Whole-genome molecular haplotyping of single cells. Nat Biotechnol 29: 51-57.
13. Peters B A, Kermani B G, Sparks A B, Alferov O, Hong P, et al. (2012) Accurate whole-genome sequencing and haplotyping from 10 to 20 human cells. Nature 487: 190-195.
14. Chan K C A, Jiang P, Zheng Y W L, Liao G J W, Sun H, et al. (2012) Cancer genome scanning in plasma: detection of tumor-associated copy number aberrations, single-nucleotide variants, and tumoral heterogeneity by massively parallel sequencing. Clin Chem 59: 211-224.
15. Swanton C (2012) Plasma-derived tumor DNA analysis at whole-genome resolution. Clin Chem. 59: 6-8.
16. Leung T Y, Vogel I, Lau T K, Chong W, Hyett J A, et al. (2011) Identification of submicroscopic chromosomal aberrations in fetuses with increased nuchal translucency and apparently normal karyotype. Ultrasound Obstet Gynecol 38: 314-319.
17. Chiu R W K, Poon L L M, Lau T K, Leung T N, Wong E M, et al. (2001) Effects of blood-processing protocols on fetal and total DNA quantification in maternal plasma. Clin Chem 47: 1607-1613.

18. Tsui N B Y, Jiang P, Chow K C K, Su X, Leung T Y, et al. (2012) High resolution size analysis of fetal DNA in the urine of pregnant women by paired-end massively parallel sequencing. PLoS One 7: e48319.
19. Zheng Y W L, Chan K C A, Sun H, Jiang P, Su X, et al. (2012) Nonhematopoietically derived DNA is shorter than hematopoietically derived DNA in plasma: a transplantation model. Clin Chem 58: 549-558.
20. Chen E Z, Chiu R W K, Sun H, Akolekar R, Chan K C A, et al. (2011) Noninvasive prenatal diagnosis of fetal trisomy 18 and trisomy 13 by maternal plasma DNA sequencing. PLoS One 6: e21791.
21. Krzywinski M, Schein J, Birol I, Connors J, Gascoyne R, et al. (2009) Circos: an information aesthetic for comparative genomics. Genome Res 19: 1639-1645.
22. Lun F M F, Tsui N B Y, Chan K C A, Leung T Y, Lau T K, et al. (2008) Noninvasive prenatal diagnosis of monogenic diseases by digital size selection and relative mutation dosage on DNA in maternal plasma. Proc Natl Acad Sci USA 105: 19920-19925.
23. Wapner R J, Martin C L, Levy B, Ballif B C, Eng C M, et al. (2012) Chromosomal microarray versus karyotyping for prenatal diagnosis. N Engl J Med 367: 2175-2184.
24. Liao G J W, Lun F M F, Zheng Y W L, Chan K C A, Leung T Y, et al. (2011) Targeted massively parallel sequencing of maternal plasma DNA permits efficient and unbiased detection of fetal alleles. Clin Chem 57: 92-101.
25. Lam K W G, Jiang P, Liao G J W, Chan K C A, Leung T Y, et al. (2012) Noninvasive prenatal diagnosis of monogenic diseases by targeted massively parallel sequencing of maternal plasma: application to beta-thalassemia. Clin Chem 58: 1467-1475.
26. van den Oever J M, Balkassmi S, Verweij E J, van Iterson M, Adama van Scheltema P N, et al. (2012) Single molecule sequencing of free DNA from maternal plasma for noninvasive trisomy 21 detection. Clin Chem 58: 699-706.

What is claimed is:

1. A method of identifying microamplifications or microdeletions in a genome of a fetus by analyzing a biological sample obtained from a female subject pregnant with the fetus, the biological sample including cell-free DNA from the fetus and from the female subject, the method comprising:
   obtaining a blood sample from the pregnant female;
   extracting plasma or serum from the blood sample to obtain the biological sample;
   obtaining, by massively parallel sequencing, one or more sequence tags for each of a plurality of DNA fragments in the biological sample;
   receiving the one or more sequence tags;
   determining, with a computer system, genomic positions for the sequence tags in a reference genome, wherein determining genomic positions for the sequence tags includes aligning the sequence tags to a reference genome;
   for each of a plurality of genomic regions:
      determining, with the computer system, a respective amount of DNA fragments within the genomic region from sequence tags having genomic positions within the genomic region;
      normalizing the respective amount to obtain a respective density; and
      comparing the respective density to a reference density to identify whether the respective density is statistically different from the reference density, wherein the genomic regions are non-overlapping;
   determining whether any of the genomic regions identified to have a respective density statistically different from the reference density is consecutive with another genomic region identified to have a respective density statistically different from the reference density, wherein each of the plurality of genomic regions is from 100 kb to 10 Mb;
   when at least N first genomic regions identified to have respective densities statistically higher than the reference density are consecutive, identifying the consecutive first genomic regions as a microamplification in the fetus, N being an integer equal to or greater than three;
   when at least N second genomic regions identified to have respective densities statistically lower than the reference density are consecutive, identifying the consecutive second genomic regions as a microdeletion in the fetus,
   wherein the plurality of DNA fragments being from 125 million to 160 million fragments achieves a diagnostic sensitivity of at least 95%.

2. The method of claim 1, wherein the biological sample is maternal blood, plasma, serum, urine, or saliva.

3. The method of claim 1, wherein N is 3.

4. The method of claim 1, wherein the genomic regions are contiguous.

5. The method of claim 1, wherein the genomic regions are of equal size.

6. The method of claim 5, wherein the size of each genomic region is about 1 Mb.

7. The method of claim 1, wherein the respective density for a genomic region is obtained by dividing the respective amount of DNA fragments for the genomic region by the total amount of DNA fragments for multiple genomic regions.

8. The method of claim 1, wherein the respective density for a genomic region equals the respective amount of DNA fragments for the genomic region.

9. The method of claim 1, wherein the reference density for a genomic region is a mean or median of a plurality of respective densities determined from one or more other biological samples not exhibiting microamplifications or microdeletions in the genomic region.

10. The method of claim 1, wherein the reference density for a genomic region is the mean or median of a plurality of respective densities obtained for other genomic regions.

11. The method of claim 1, wherein each of the plurality of genomic regions has a size from 1 Mb to 10 Mb.

12. The method of claim 1, further comprising:
   displaying, by the computer system, a first result identifying the consecutive first genomic regions as comprising a microamplification in the genome of the fetus when at least N first genomic regions identified to have respective densities statistically higher than the reference density are consecutive, and
   displaying, by the computer system, a second result identifying the consecutive second genomic regions as comprising a microdeletion in the genome of the fetus when at least N second genomic regions identified to have respective densities statistically lower than the reference density are consecutive.

13. The method of claim 1, wherein the plurality of DNA fragments includes at least one million DNA fragments.

14. The method of claim 1, wherein the genomic regions are determined before determining amounts of DNA fragments.

15. The method of claim 1, wherein:
the plurality of DNA fragments is from 125 million to 160 million fragments to achieve a diagnostic sensitivity of at least 95%, and
each of the plurality of genomic regions has a size from 1 Mb to 10 Mb.

16. The method of claim 1, wherein obtaining the one or more sequence tags includes paired-end sequencing of each of the plurality of DNA fragments.

17. The method of claim 1, further comprising:
when less than N first genomic regions identified to have respective densities statistically higher than the reference density are consecutive, not identifying the consecutive first genomic regions as a microamplification, and
when less than N second genomic regions identified to have respective densities statistically lower than the reference density are consecutive, not identifying the consecutive second genomic regions as a microdeletion.

18. The method of claim 17, wherein obtaining the one or more sequence tags includes paired-end sequencing of each of the plurality of DNA fragments.

19. The method of claim 1, wherein the plurality of DNA fragments being from 125 million to 160 million fragments achieves a diagnostic specificity of at least 99%.

20. The method of claim 1, wherein the plurality of DNA fragments is from 125 million to 160 million fragments.

21. A method of identifying microamplifications or microdeletions in a genome of a fetus by analyzing a biological sample obtained from a female subject pregnant with the fetus, the biological sample including cell-free DNA from the fetus and from the female subject, the method comprising:
obtaining a blood sample from the pregnant female;
extracting plasma or serum from the blood sample to obtain the biological sample;
obtaining, by massively parallel sequencing, one or more sequence tags for each of a plurality of DNA fragments in the biological sample;
receiving the one or more sequence tags;
determining, with a computer system, genomic positions for the sequence tags in a reference genome, wherein determining genomic positions for the sequence tags includes aligning the sequence tags to a reference genome;
for each of a plurality of genomic regions:
determining, with the computer system, a respective amount of DNA fragments within the genomic region from sequence tags having genomic positions within the genomic region;
normalizing the respective amount to obtain a respective density; and
comparing the respective density to a reference density to identify whether the respective density is statistically different from the reference density, wherein the genomic regions are non-overlapping;
determining whether any of the genomic regions identified to have a respective density statistically different from the reference density is consecutive with another genomic region identified to have a respective density statistically different from the reference density, wherein each of the plurality of genomic regions is from 100 kb to 10 Mb;
when at least N first genomic regions identified to have respective densities statistically higher than the reference density are consecutive, identifying the consecutive first genomic regions as a microamplification in the fetus, N being an integer equal to or greater than three;
when at least N second genomic regions identified to have respective densities statistically lower than the reference density are consecutive, identifying the consecutive second genomic regions as a microdeletion in the fetus,
wherein the method is capable of achieving a diagnostic sensitivity of 95% for the plurality of DNA fragments equal to 125 million fragments when each of the plurality of genomic regions is 1 Mb.

22. A method of identifying microamplifications or microdeletions in a genome of a fetus by analyzing a biological sample obtained from a female subject pregnant with the fetus, the biological sample including cell-free DNA from the fetus and from the female subject, the method comprising:
obtaining a blood sample from the pregnant female;
extracting plasma or serum from the blood sample to obtain the biological sample;
obtaining, by massively parallel sequencing, one or more sequence tags for each of a plurality of DNA fragments in the biological sample;
receiving the one or more sequence tags;
determining, with a computer system, genomic positions for the sequence tags in a reference genome, wherein determining genomic positions for the sequence tags includes aligning the sequence tags to a reference genome;
for each of a plurality of genomic regions:
determining, with the computer system, a respective amount of DNA fragments within the genomic region from sequence tags having genomic positions within the genomic region;
normalizing the respective amount to obtain a respective density; and
comparing the respective density to a reference density to identify whether the respective density is statistically different from the reference density, wherein the genomic regions are non-overlapping;
determining whether any of the genomic regions identified to have a respective density statistically different from the reference density is consecutive with another genomic region identified to have a respective density statistically different from the reference density, wherein each of the plurality of genomic regions is from 100 kb to 10 Mb;
when at least N first genomic regions identified to have respective densities statistically higher than the reference density are consecutive, identifying the consecutive first genomic regions as a microamplification in the fetus, N being an integer equal to or greater than three;
when at least N second genomic regions identified to have respective densities statistically lower than the reference density are consecutive, identifying the consecutive second genomic regions as a microdeletion in the fetus,
wherein the plurality of DNA fragments being from 240 million to 480 million fragments achieves a diagnostic sensitivity of at least 99%.

* * * * *